United States Patent [19]
Krog et al.

[11] Patent Number: 5,312,343
[45] Date of Patent: May 17, 1994

[54] DEVICE FOR SEGMENTAL PERFUSION AND ASPIRATION OF COLON AND RECTUM

[75] Inventors: Michael Krog, Engelbrektsgatan 4, S-803 24 Gävle; Roger Hällgren, Dragontorpsvägen 9, S-740 22 Bälinge; Lars Knutson, Upsala; Yngve Raab, Cellovägen 124 E, S-756 54 Uppsala, all of Sweden

[73] Assignees: Michael Krog, Gävle; Roger Hällgren, Bälinge; Yngve Raab, Upsala, all of Sweden

[21] Appl. No.: 867,205

[22] PCT Filed: Nov. 23, 1990

[86] PCT No.: PCT/SE90/00773
§ 371 Date: Jul. 2, 1992
§ 102(e) Date: Jul. 2, 1992

[87] PCT Pub. No.: WO91/08013
PCT Pub. Date: Jun. 13, 1991

[30] Foreign Application Priority Data
Nov. 24, 1989 [SE] Sweden ............... 89-03980-4

[51] Int. Cl.⁵ ............................................. A61M 29/00
[52] U.S. Cl. .................................... 604/101; 604/102; 606/197
[58] Field of Search ............... 604/96, 101, 102; 606/191, 192, 197

[56] References Cited

U.S. PATENT DOCUMENTS 4,180,076 12/1979 Betancourt .
4,368,739 6/1983 Nelson, Jr. .
4,484,579 11/1984 Meno et al. ............... 604/101 X
4,527,549 7/1985 Gabbay ..................... 604/101 X
4,983,167 1/1991 Sahota ....................... 606/194

FOREIGN PATENT DOCUMENTS 2652495 4/1991 France ...................... 606/197
8803389 5/1988 World Int. Prop. O. .

Primary Examiner—C. Fred Rosenbaum
Assistant Examiner—Corrine Maglione
Attorney, Agent, or Firm—Browdy and Neimark

[57] ABSTRACT

The present invention concerns a device for segmental perfusion/aspiration of intestinal segments, including a catheter (1) having one large central channel (10) and several parallel, in relation to the central channel smaller channels (11-21) which, through holes in the outer wall of the catheter, are used for inflation of segment-delimiting balloons arranged along the catheter and around its circumference, for aspiration and perfusion of fluid from and to different segments of the intestine delimited by balloons, and for release of marker substance. The invention is characterized by that the device is shaped for introduction through the anal orifice, that the device includes two intestinal segments which are delimited by four inflatable balloons, that the device is provided with an anchoring device (2), which after introduction of the catheter is inflated in order to firmly fix the catheter to the anal orifice, and that the central channel is designed to receive an endoscope.

8 Claims, 5 Drawing Sheets

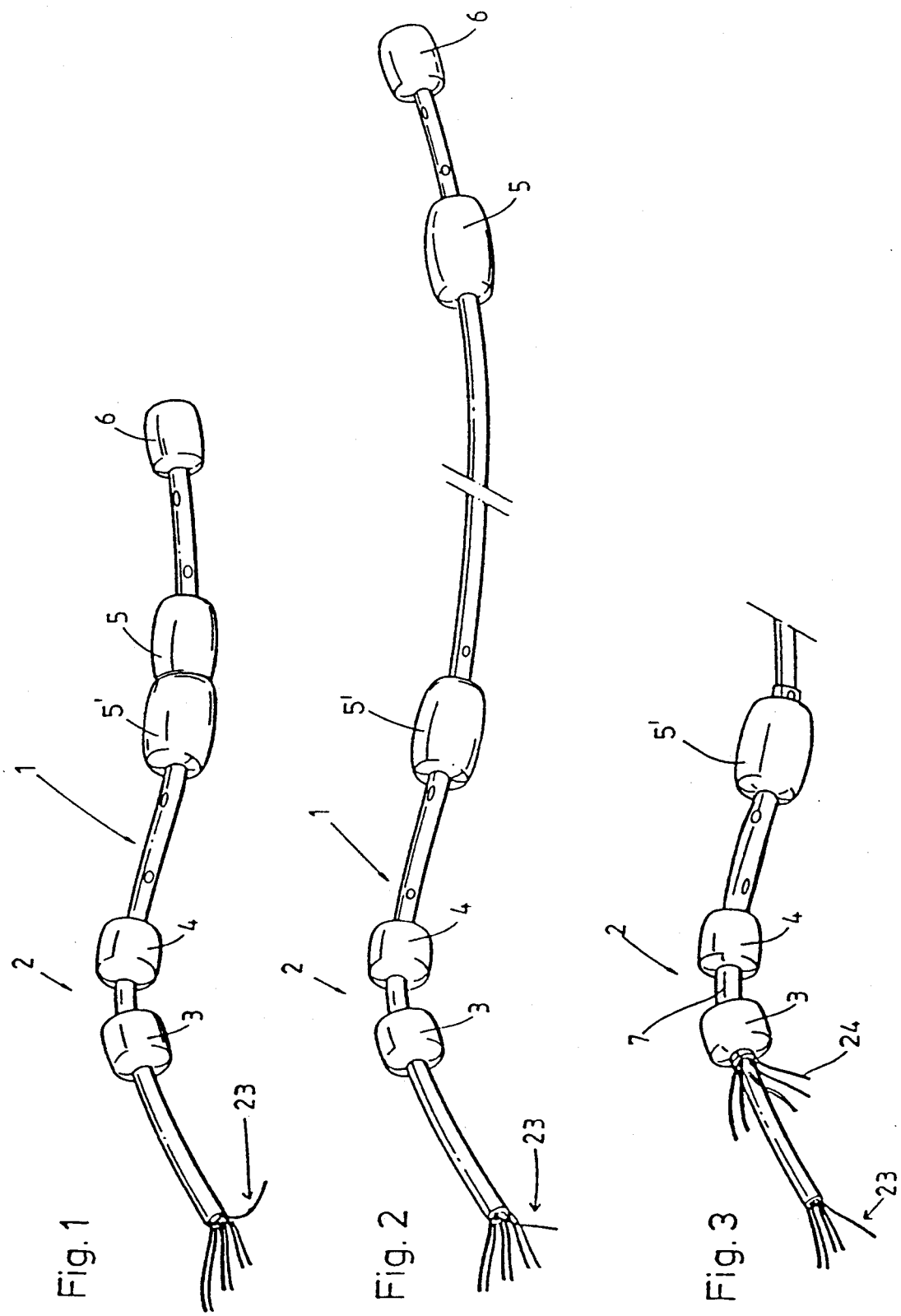

DEVICE FOR SEGMENTAL PERFUSION AND ASPIRATION OF COLON AND RECTUM

The present invention concerns a technique for the diagnosis of disease and also pharmacokinetic studies of the colon and rectum based on analyses of cells, secretions and intestinal fluids achieved by perfusion/aspiration of the large intestine by neutral or provocative fluids and a device for performing this procedure. The invention also concerns a procedure for local treatment of diseases in the large intestine.

A refined diagnostic technique of disease in the large intestine with the prospect of identifying inflammatory and other mediators which are released from or through the intestinal wall is not at hand. The diagnostic methods today are based on x-ray, endoscopy and examination of tissue specimens taken in connection with endoscopy or surgery. These methods are limited by the fact that certain mediators cannot be measured. Open systems with dialysis bags in rectum can measure certain mediators but only those with a small molecular size.

An example of a situation where improved diagnostic techniques could be valuable is in the preoperative investigation of patients with inflammatory bowel disease. The pouch procedure, where a reservoir of the small intestine is prepared when the diseased large intestine has been removed, is the surgical treatment of choice in ulcerative colitis. However, if a patient with Crohn's disease located to the large intestine is treated with the same procedure this will inevitably lead to recurrent disease and a situation where the reservoir has to be removed. With a loss of vital part of intestine a risk of dangerously short bowel can occur. With currently available techniques it is difficult to separate these diseases in 20-30% of the cases.

Another situation where a system for segmental perfusion is useful is in the study of the release of pharmacologic substances in the large intestine. Many substances for treatment of disease of the large intestine are taken by the oral route but not released until it reaches the target organ. By measuring concentrations of pharmacological preparations in closed segments of the large intestine new possibilites of testing these preparations will appear.

A third application is the local treatment of diseases in the large intestine. Drugs can be given as local treatment, i.e. enemas or suppositories. However, when the disease is localised to certain parts of the intestine either low concentrations in the involved area or risk of side effects with higher doses are problems not possible to solve with the presently available administration forms.

The invention makes it possible to give doses with high local concentrations in the involved area of a closed segment without risking dangerous side effects.

Perfusion and aspiration studies from the small intestine with analysis of intestinal contents of inflammatory markers has been described in SE B 455 368, which refers to a catheter for intestinal use, not including the large intestine. The construction of the known catheter makes this application impossible. This catheter is 1.6 m long and is introduced through the mouth or nose. A catheter introduced by the oral route aimed for investigations of the large intestine has to be very long (6 meters or more), still flow in the channels would not be possible because of high flow resistance depending on channel length and the consistency of secretions from the large intestine. The jejunal catheter cannot be introduced by the anal route as this should imply blind introduction into the intestinal tract against peristalsis with risk for intestinal damage. The catheter would also be expelled by the peristaltic wave as it is to weak and lacks an anchoring device.

The purpose of the present invention is to improve diagnostic accuracy, to study the local effect of pharmacological preparations given orally or rectally and to increase the possibilites of giving potent treatment to localised disease processes and thereby avoiding serious side effects. To achieve these goals the following requirements have to be fulfilled:

1. A physiologically closed segment of the large intestine has to be established,
2. The segment must not be expelled by the normal peristaltic waves but stay in its predetermined position throughout the investigation/treatment period,
3. The segment must be able to receive and offer a quantative exchange of perfusion fluid,
4. The physiologically normal passage of intestinal fluids and gas has to be allowed to pass the segment avoiding discomfort to the subject and leaving the intestinal segment under study/treatment undisturbed.

A perfusion system of this kind, fulfilling demands on safety and comfort for the subject under study/treatment, can be achieved by a device according to the patent claims.

In the following the invention will be described in further detail in connection with the enclosed drawings, in which FIG. 1 is a schematic view of a catheter according to the invention designed for the left part of the large intestine and the rectum;

FIG. 2 is a schematic view of a catheter according to the invention designed for the right part of the large intestine and the rectum;

FIG. 3 is a partial schematic view of an alternative embodiment of the catheter according to the invention, where an anchoring device and a segment delimiting balloon are displacably arranged on the outer wall of the catheter;

Figure 4:
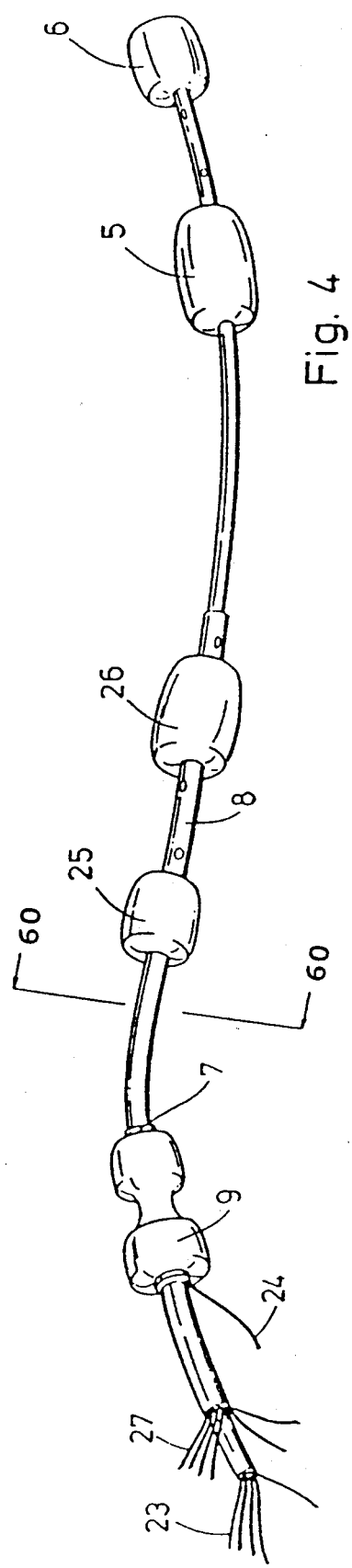
FIG. 4 is a schematic view of another alternative embodiment of a catheter according to the invention.

In the figures the catheter according to the invention is generally assigned with the reference numeral 1. The catheter is made of polyvinyl chloride alternatively polyurethane and the catheter is made stiffer in its inner part. The inner diameter can vary between 11 and 17 mm and the outer diameter between 15 and 21 mm. The catheter wall is provided with channels, which will be described below. FIG. 1 shows a catheter suited for studies of the left part of the large intestine with an upper (colonic) and a lower (rectal) segment. The segments are established after positioning of the catheter and inflation of the balloons deliminating the segments. The length of the catheter is 60-65 cm. In FIG. 2 a catheter for the right part of the large intestine with an upper (colonic) and a lower (rectal) segment is shown. The length of this catheter is 120-125 cm. The catheter according to FIG. 2 is distinguished from the catheter in FIG. 1 by a longer distance between the segments. It is understood that it is possible to vary the distance between the segments from 0 to 60 cm. The catheter can then be used for investigation of two segments at the same time, the upper segment can then be positioned at different levels in the large intestine.

The catheter is provided with an anchoring device 2, with which the catheter can be attached to the anal orifice after that the catheter has been brought into position in the intestine. The anchoring device includes two inflatable balloons 3 and 4, which are about 4 cm long, 4 cm in diameter and placed 4 cm apart. Furthermore, the catheter is provided with three additional inflatable balloons 5', 5 and 6, which are about 7, 7 and 5 cm long, respectively, 4 cm in diameter and positioned so that segments with a length of 8 cm will be formed. The balloons 5' and 5 form the upper and lower limit of the rectal and colonic segments, respectively, while balloon 6 constitutes the upper limit of the colonic segment. The distance between the segments can vary between 0 to 60 cm according to the data mentioned above. The balloons are glued or by other means attached to the catheter 1. At the position for the balloons and at other positions along the catheter separate channels terminate in holes (not shown) in the catheter wall. These channels extend longitudinally of the catheter and their end attachments are generally shown by the the reference numeral 23. It is appreciated that the number of end attachments are the same as the number of channels used in catheter 1. Channels for marker substances terminate in holes above the segments.

In the embodiment according to FIG. 3 the anchoring device 2 and the lower segment, which is delimited by the balloons 4 and 5', are movable on the catheter 1, allowing the distance between the upper and lower segments to be varied. The anchoring device 2 and the balloon 5' are attached to a short tube 7, which can slide on the catheter 1. Furhermore, it is shown that separate channel connections 24 go to the tube 7 for inflation of the balloons 3 and 4 of the anchoring device, the rectal segment balloon 5', for perfusion/aspiration of the segment and for marker substance above the segment. The tube part 7 can be attached to the catheter 1 in any convenient way.

FIG. 4 shows an alternative embodiment of the catheter according to the invention. In this embodiment the anchoring device 2, including the tube 7, is movable on the outer wall of a tube 8, which in turn is movable on the outer wall of the catheter 1. Here is the anchoring device 2 formed as a dumbbell 9 but it could also be formed as two separate balloons 3, 4 according to FIG. 1, 2 and 3. The movable tube 8 is provided with two inflatable balloons 25, 26. This design makes it possible to vary the distance between the segments as well as the distance between the lower segment and the anchoring device. Separate connections 27 are arranged for the channels in tube 8, which are aimed for air to the balloons 25, 26 and for perfusion/aspiration of fluid to and from the segment formed by the balloons 25 and 26. The fifth channel is used for delivering marker substance above the segment. The catheter 1 is as previously described provided with the balloons 5, 6. It is understood that the number of balloons on the tube 8 and the catheter 1 can be varied.

After inserting the catheter to the predetermined position in the large intestine, the tube 7 is attached to tube 8, which in turn is attached to catheter 1, which can be achieved in the way previously mentioned. It is understood that the anchoring device 2 also can be fixed to the tube 8. The separate channel connection 24 is then included in the channel connections 27.

Figure 5:
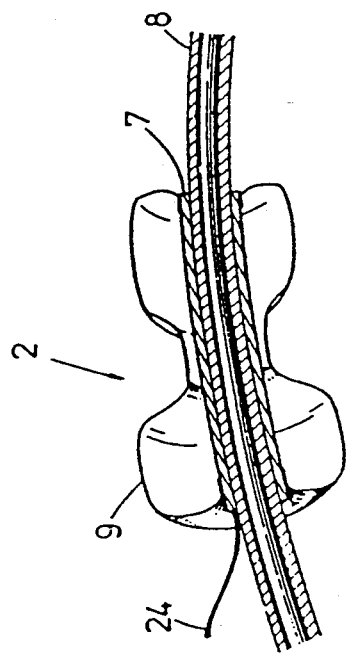
FIG. 5 is a cross-sectioned view of the anchoring device for the catheter according to the FIG. 4.

In FIG. 5 a view in more detail is shown of the anchoring device 2 in the dumbbell form. The anchoring device 2, i.e. the dumbbell 9, is here formed in one piece instead of the two separate balloons 3 and 4. For this only one air connection 24 to a channel in tube 7 will be needed.

Figure 6:
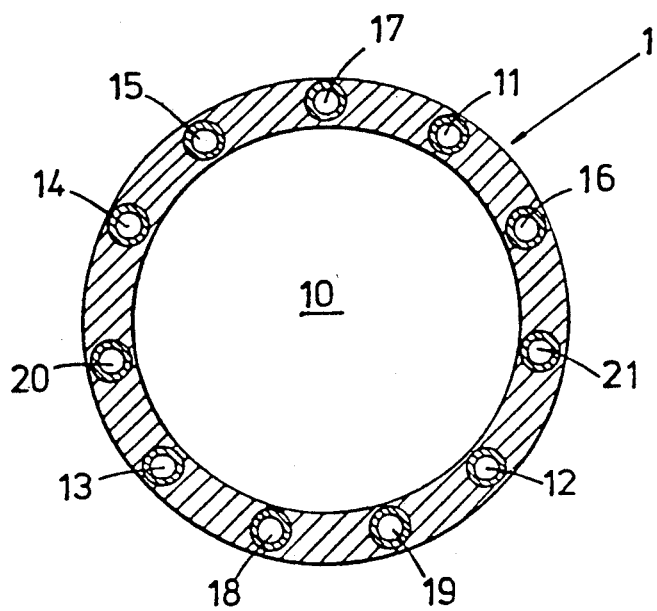
FIG. 6 is a cross section through the catheter shown in FIGS. 1 and 2.

In FIG. 6 a cross section of the catheter in FIGS. 1 and 2 is shown. The lumen of the catheter is a wide central channel 10, in which an endoscope is introduced for positioning of the catheter and later used for drainage of air and intestinal contents coming from the part of the intestine lying above the catheter.

The shown embodiments of the catheter have five to eleven channels in the wall of the catheter. The catheter according to FIGS. 1 and 2 has four or five air channels 11-15 terminating in holes leading into the balloons (four if an anchoring device formed as a dumbbell is used, five if two separate balloons are used). Furthermore, the catheter has two perfusion channels 16 and 18 which terminate in holes leading into the segments formed after positioning of the catheter and inflating the balloons. There are also two channels for aspiration which terminate in holes leading into the segments. The catheter has an indication channel 20, which terminates in a hole above the balloon 6 for the delivery of marker substance above the segment for the detection of leakage from the intestine above the segment. The indication channel can also be used for perfusion of pharmacological drugs. When the segments are placed at a distance from each other there is also an indication channel 21 terminating in a hole above the lower segment.

Every channel terminates in holes leading to the balloons and to the different segments. Thus, a flow path is established between the end connections 23, 24, 27 and said catheter holes. The indication channel terminates in a hole above the segments. After every hole (apart from the indication channels) the channels are plugged in order to facilitate cleaning of the channels.

The balloons are made of latex and the pressure is well below the lowest blood pressure (30-40 mm Hg). It is very important to avoid pressure damages to the intestinal wall. With the low pressure in the balloons according to the invention, it is possible to have the catheter in position for long periods of time without risking damage to the intestinal wall.

The connections for the channels are supplied with automatically tightening Luer lock attachments and also have pressure balloons for the channels leading to the segment balloons. It is possible to provide the air channels with pressure alarms for supervision of of the pressure in the balloons.

Figure 7:
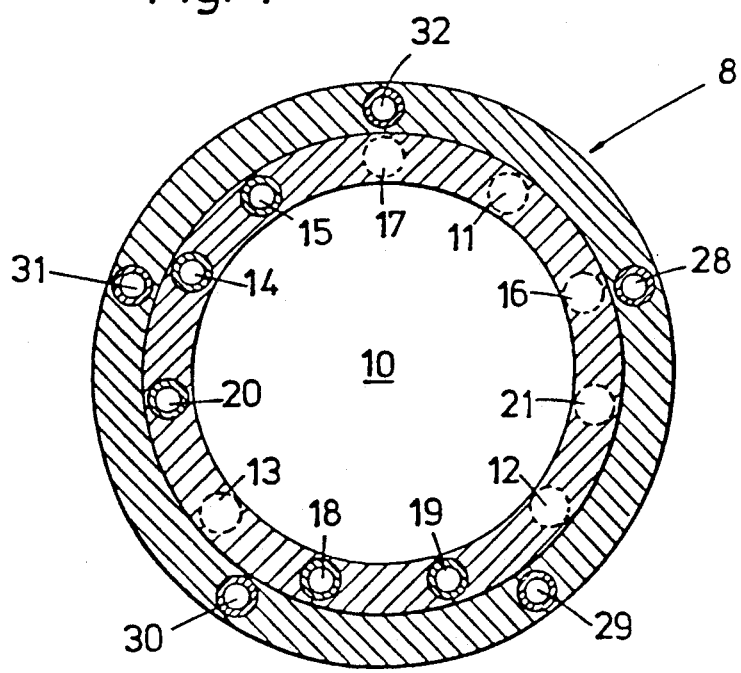
FIG. 7 is a cross section along line 60—60 in FIG. 4.

FIG. 7 is a cross section along a line 60—60 of the catheter shown in FIG. 4. The outer tube 8 is provided with five channels; 28 and 29 for air to balloons 25 and 26 and 30 and 31 for perfusion/aspiration of the segment formed by the balloons 25 and 26. The fifth channel 32 is an indication channel which ends above the segment. The channels in the catheter 1 correspond to the earlier described channels, where five (14, 15, 18, 19 and 20) are used for air, perfusion/aspiration and indication substance to the upper segment. Channels not used are shown with interrupted lines in the figure. In the embodiment according to FIGS. 4-5, a separate channel 24 to the tube 7 for air to the anchoring device is required.

Along the whole length of the catheter there is an X-ray marker (not shown) to facilitate identification fluoroscopically when the catheter is placed into position. The test segments are indicated with special X-ray markers (not shown).

Figure 9:
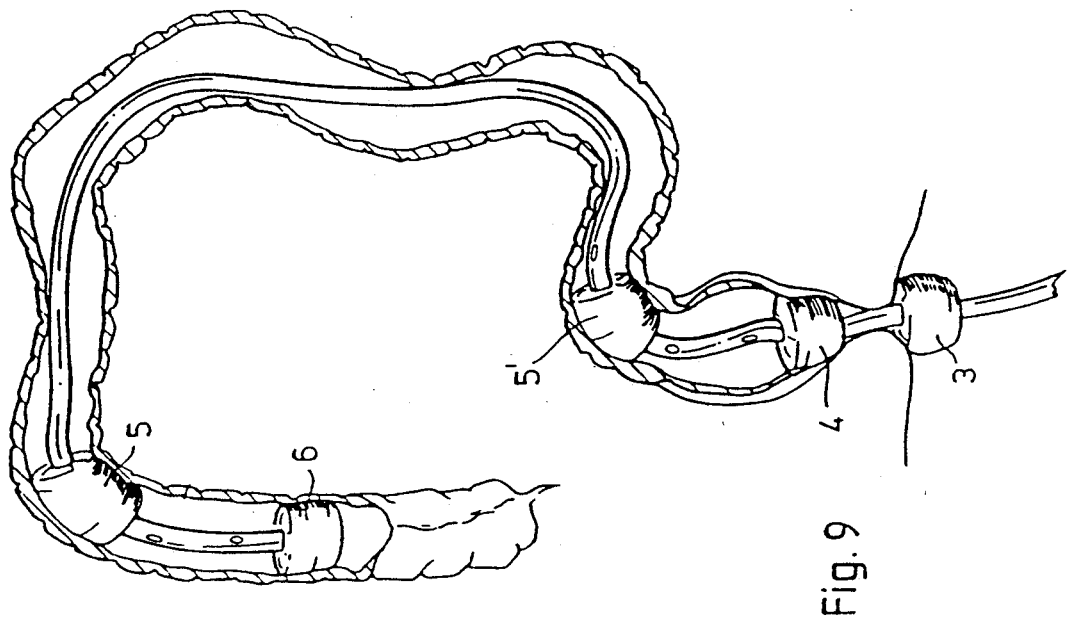
FIG. 9 shows the catheter according to FIG. 2 when it has been brought into position in the large intestine.
Figure 8:
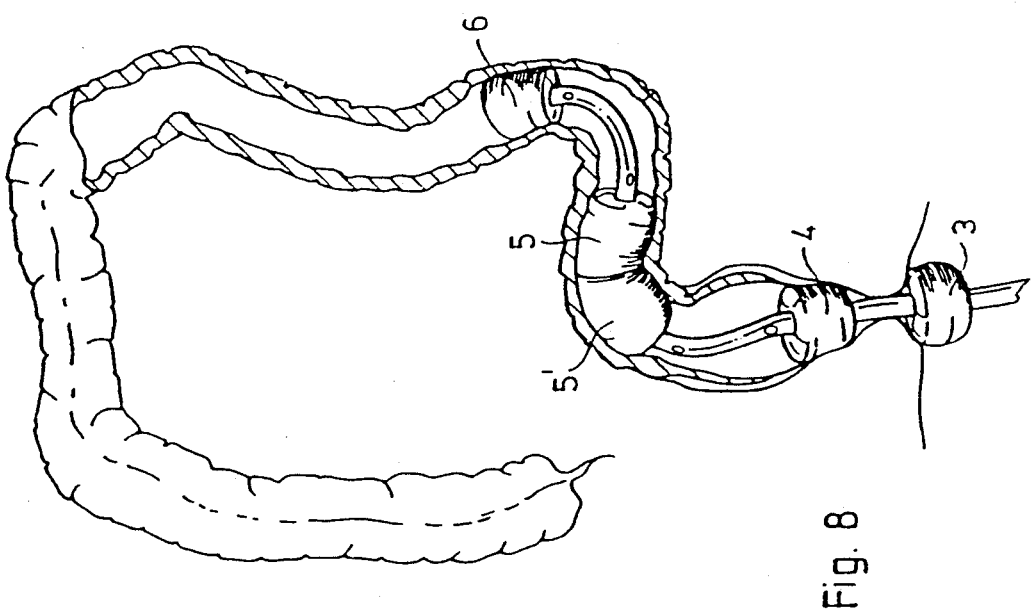
FIG. 8 shows the catheter according to FIG. 1 when the catheter has been brought into position in the large intestine.

Finally the positioning the catheter in the large intestine is shown in FIGS. 8-9. FIG. 8 shows the catheter according to FIG. 1. In FIG. 9 the catheter according to FIG. 2 is shown.

Figure 6A:
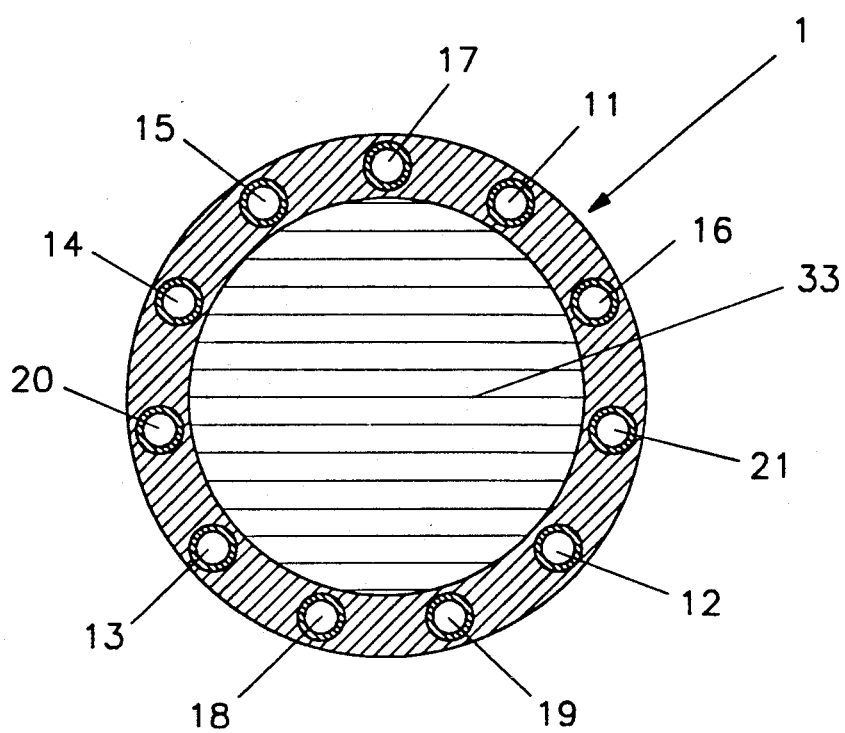
FIG. 6A shows a cross section of the catheter of FIGS. 1 and 2 further including an endoscope schematically depicted and fixed within the central channel of the catheter.

In an alternative embodiment, shown in FIG. 6a an endoscope 33 is firmly fixed or fused to the inner walls of the central channel 10 of the catheter 1. The endoscope then remains in the large intestine during the whole procedure. Gas and other intestinal contents can then be cleared through a suction canal in the endoscope.

The endoscope 33 is a conventional one and comprises a light source, and channels for suction, flushing and instrumentation.

In the following the procedure according to the invention will be illustrated in the form of an example.

To perform an investigation with the use of a catheter for the large intestine according to the invention, an endoscope is put through the central channel 10 of the catheter. When the endoscope has been introduced through the anal orifice it is manouvered under direct vision to the predetermined position for the examination. When the position has been checked fluoroscopically or by other means the catheter is introduced and the endoscope then will act as conductor for the catheter. The endoscope is then withdrawn and the central channel will act as a channel for drainage of air and other intestinal contents coming from the part of the intestine above the upper segment of the catheter. In the alternative embodiment in which the catheter 1 is fixed or fused to the endoscope it remains in position after introduction to the predetermined position. The suction channel in the endoscope then clears gas and intestinal fluids above the catheter. When the catheter has been placed in position, the balloons of the anchoring device 2 and the segment balloons are inflated through the above mentioned channels. The lower part of the anchoring device (balloon 3 or the lower part of the dumbbell) is located outside the anal orifice. The upper part of the anchoring device (balloon 4 or the upper part of the dumbbell) is located in the lower part of rectum, just above the anal sfincter (FIGS. 8 and 9).

The catheter is made in two main versions, one for examination of the left part of the large intestine and one for the right part. An alternative and very useful design of the catheter according to the invention, is one shown in FIG. 4 where the catheter 1 and the tube 8 each are provided with a balloon-deliminated segment. With this design it is possible to establish closed segments at optional levels in the large intestine.

As the catheter has several balloons with at least two separate segments, the pressure will be evenly distributed in different parts of the intestine. Therefore, the peristaltic waves of the intestine will pass the catheter system and not expel it through the rectum. Before examination the segments are rinsed with saline to eliminate residual intestinal contents. Two segments have been formed which constitute at least two biologically closed parts of rectum and colon depending on how many delimiting balloons are used. Biologically closed is defined as a space not hermitically closed but a geometrically deliminated part of the rectum/colon under physiological conditions. This means that intestinal contents outside the segments can be drained through the central channel thereby not disturbing analyses based on examinations from the segments. In this way it is possible to perform very accurate analyses of cells, secretions or other substances released from the intestine wall to its lumen. It also makes it possible to add to the perfusion fluid pharmacological substances which protect or inhibit cells or secretions released from the intestinal wall to the perfusion fluid. By administering pharmacological or other chemical compounds in one segment it is possible to perform refined measurements of various effects in the other segment. This is important in pharmacokinetic studies. Finally, by enclosing a diseased segment, e.g. malignant processes, it is possible to give localized high doses of pharmacological agents without risking serious side effects.

We claim:

1. A device for segmental perfusion/aspiration of intestinal segments comprising;

a catheter (1) having a wall forming a large central channel (10), said large central channel (10) sized for passage of an endoscope therethrough, a plurality of parallel smaller channels (11-21) in said wall having diameters smaller than a diameter of said central channel, said plurality of smaller channels each having a first end terminating at a hole on an outer surface of said wall, a plurality of intestinal segment-deliminating balloons which pairwise delimit said segments, said plurality of balloons sealingly engaged along a length of said catheter and around a circumference thereof, a number of holes of said plurality of holes communicating with an interior of said plurality of segment-deliminating balloons to permit inflation thereof through a corresponding number of said plurality of parallel smaller channels, a remainder of said plurality of holes providing aspiration and perfusion of fluid from and to different segments of an intestine delimited by pairs of said plurality of segment-deliminating balloons and release of a marking substance to selected segments of said different segments through a corresponding number of said plurality of parallel smaller channels, said device being sufficiently stiff for introduction through an anal orifice and having an inflatable anchoring device (2) engaged on an end of said catheter to firmly fix said end on two sides of said anal orifice after inflation, wherein said device produces at least two of said different segments delimited by said intestinal segment-deliminating balloons, and wherein said anchoring device is formed by two balloons (3, 4).

2. A device according to claim 1, wherein said two balloons (3, 4) are spaced apart on said catheter and separately inflatable.

3. A device according to claim 1, further comprising, a tube (7) slideably engaged over said outer surface of said wall, said anchoring device (2) and an intestinal segment-deliminating balloon (5') mounted around a circumference of said tube (7), said tube permitting adjustment of a longitudinal distance between said segment-deliminating balloon mounted on said tube and said plurality of segmented-deliminating balloons engaged on said catheter, said tube having a plurality of channels each having an end terminating in a hole on a surface of said tube, for respective inflation of said anchoring device (2), said balloon (5') and for aspiration/perfusion of fluid from and to a segment of said intestine delimited by said anchoring device (2) and said balloon (5') and for releasing marker substance proximal of said segment.

4. A device according to claim 1 further comprising, a first tube (8) slideably engaged over said outer surface of said wall, said first tube having two balloons (25, 26) delimiting a first segment of said intestine, a second tube (7) having said anchoring device (2) mounted thereon and slideably engaged over said first tube (8), and said catheter (1) having two balloons (5, 6) delimiting a second segment of said intestine.

5. A device according to claim 4, comprising channels (28-32) terminating at holes in said first tube (8) for inflating said balloons (25, 26) thereon and, perfusing and aspirating fluid to and from said first segment delimited by said two balloons on said first tube (8) and for releasing of a marker substance proximal of said first segment.

6. A device according to claim 5, comprising at least one additional channel on said second tube (7) communicating with an interior of said anchoring device (2) for inflation thereof.

7. A device according to claim 1, wherein an endoscope is firmly fixed or fused to an inner wall of said central channel (10).

8. A process for segmental perfusion/aspiration of internal segments in the large intestine, comprising the steps of:

(a) inserting an endoscope by means of a catheter through the anal orifice into the large intestine;

wherein said catheter comprises a wall forming a large central channel (10), within which said endoscope is integrally engaged, said wall having a plurality of parallel channels (11-21) formed therein, said plurality of channels each having a first end terminating at a hole on an outer surface of said wall, a plurality of balloons sealingly engaged along a length of said catheter and around a circumference thereof, a number of holes of said plurality of holes communicating with an interior of said plurality of balloons, and an inflatable anchoring device engaged on an end of said catheter;

(b) inflating said anchoring device to firmly fix said catheter to an anal orifice; and (c) thereafter inflating pairs of said balloons on said catheter to form intestinal segments, and perfusing and aspirating said intestinal segments through a remainder of said plurality of holes.

* * * * *